United States Patent [19]
Ban et al.

[11] Patent Number: 5,106,636
[45] Date of Patent: Apr. 21, 1992

[54] METHOD OF CONTROLLING THE QUALITY OF DOUGH DURING ITS PROCESSING

[75] Inventors: Nobuo Ban; Toshiichi Ozawa, both of Utsunomiya, Japan

[73] Assignee: Rheon Automatic Machinery Co., Ltd., Utsunomiya, Japan

[21] Appl. No.: 624,180

[22] Filed: Dec. 7, 1990

[30] Foreign Application Priority Data

Dec. 12, 1989 [JP] Japan .................................. 1-321932

[51] Int. Cl.⁵ ...................... A21D 8/00; G01N 33/00
[52] U.S. Cl. ................................. 426/231; 426/502; 426/517
[58] Field of Search ...................... 426/231, 502, 517

[56] References Cited

U.S. PATENT DOCUMENTS 4,849,234  7/1989  Spinelli et al. .................. 426/231
4,877,623  10/1989  Hayashi ............................ 426/231

Primary Examiner—George Yeung
Attorney, Agent, or Firm—Guy W. Shoup; David W. Heid

[57] ABSTRACT

A method is provided of controlling the quality of dough during its processing, in which the physical properties of portions of a dough strip being continuously fed are automatically and continuously measured, to obtain the specific weight calculated from the dimensional and weight data, of each of the portions of the dough strip, so that the dimensional data and specific weight can be used for processing the dough mass and for formulating raw materials for the next lot to be produced, and in which method, based on the obtained specific weight, the thickness of a dough piece having a uniform top surface area to be stamped out by a puncher is automatically calculated by a computer and an additional stretching system adjusts the thickness of the dough strip, so that the weight of a stamped-out dough piece is automatically made uniform during the operation.

3 Claims, 2 Drawing Sheets

F I G. 2
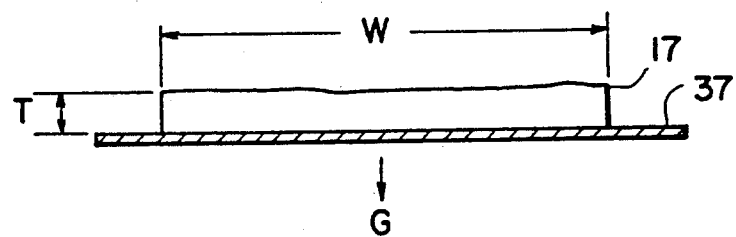
F I G. 3
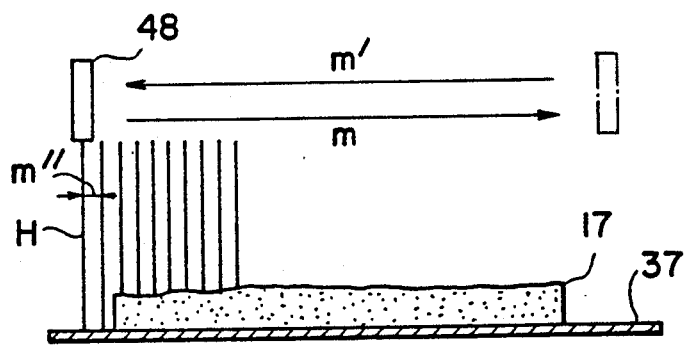
F I G. 4
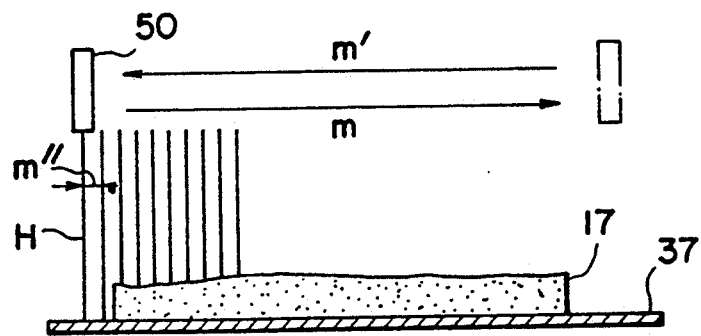

METHOD OF CONTROLLING THE QUALITY OF DOUGH DURING ITS PROCESSING

BACKGROUND OF THE INVENTION

1. Field of Invention

This invention relates to a method of controlling the quality of dough or other similar viscoelastic materials. It particularly relates to a method of continuously inspecting the physical properties of a strip of dough or other similar viscoelastic materials being continuously fed, thereby obtaining information on the formulation of the raw materials, and controlling the quality of the viscoelastic materials during their processing.

2. Description of Prior Art

The quality of bread or confectionery products depends on the formulation and kneading conditions of the raw materials. Conventionally, these products have been inspected when the final and individual product is finished. Therefore, if, for example, the specific weight of the dough changes due to a change in the fermenting conditions, inferior products, where the weight per unit product is not uniform, are produced. No technique for automatically and continuously inspecting and measuring the physical properties of dough or other viscoelastic materials for foodstuffs, while they are being produced, and using the measured data for formulating the raw materials and adjusting the physical properties of viscoelastic materials for foodstuffs, has been known in the art.

SUMMARY OF THE INVENTION

Therefore an object of this invention is to provide a method of controlling the quality of the dough that comprises continuously measuring the thickness, width, and weight of portions of a dough strip being continuously fed, to obtain the specific weight, calculated from the dimensional and weight data, of each portion of the dough strip, thereby using this data for formulating and processing said dough.

Another object of this invention is to provide a method of controlling the quality of the dough that comprises continuously measuring the thickness, width, and weight of portions of a dough strip being continuously fed from a first stretching system, to obtain the specific weight, calculated from the dimensional and weight data, of each of said portions of said dough strip, and adjusting the thickness of said dough strip to a certain value so as to make uniform the weight of a dough piece of a uniform top surface area.

By this invention the physical properties, namely, thickness, width, and weight of portions of a dough strip being continuously fed, are continuously measured. In so doing the specific weight of each portion is also obtained. The thus-obtained physical data, namely, the thickness, width, and specific weight, are used for formulating raw materials for the dough so that the formulating ratio or kinds of raw materials for the next lot to be produced are corrected.

By this invention the thickness of a dough piece to be stamped out from the dough strip of a uniform top surface area is calculated based on the obtained specific weight, the top surface area, and a predetermined weight of the dough piece. Therefore, if the specific weight values measured momentarily fluctuate, the calculated thickness values will also fluctuate in response to the specific weight values measured. Therefore, if the specific weight measured is greater than a reference value of the specific weight, the thickness of the dough strip is then adjusted, by a stretching system, to have a value smaller than the reference value of the thickness, and vice versa. Thus, the weight of a stamped-out dough piece is automatically made uniform during the operation in spite of the fluctuation in the specific weight.

BRIEF DESCRIPTION OF THE DRAWINGS

FIG. 2 is a transverse sectional view of a dough strip, illustrating how to measure its specific weight.

FIG. 3 is a schematic and elevational view illustrating how to measure the thickness of a dough strip, in an embodiment of this invention.

FIG. 4 is a schematic and elevational view illustrating how to measure the width of a dough strip, in an embodiment of this invention.

DESCRIPTION OF THE PREFERRED EMBODIMENTS

Figure 1:
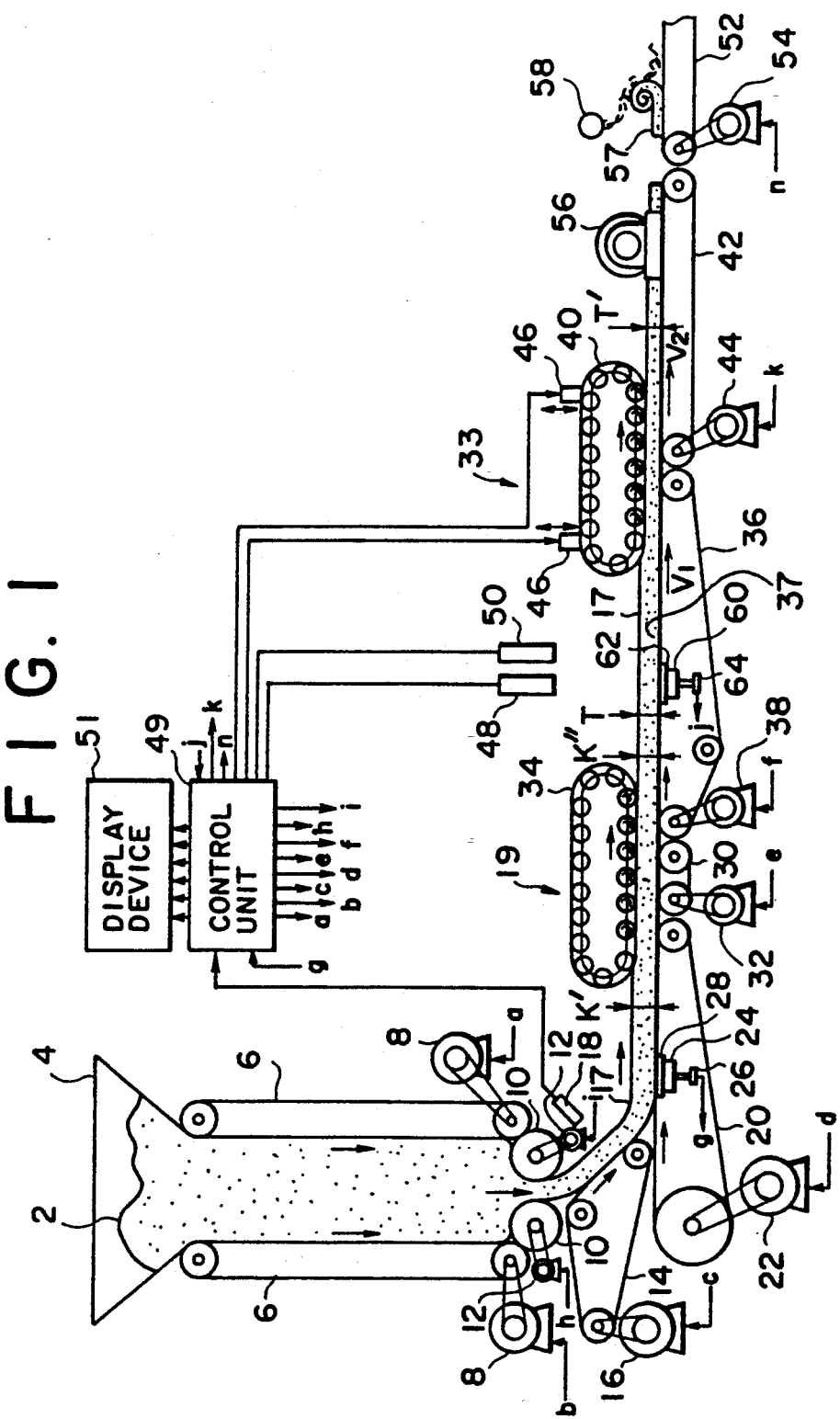
FIG. 1 is a schematic side-elevational view, partly in section, illustrating an embodiment of this invention.

A first embodiment of this invention will now be explained by reference to the drawings.

First, an apparatus for working the method of this invention will be explained.

In FIG. 1, vertical conveyors (6, 6) for vertically conveying dough (2) are provided under a hopper (4). They are driven by motors (8, 8). The space between the conveyors (6, 6) constitutes a passage for dough (2). Adjacent the lowest parts of the vertical conveyors (6, 6) outlet rollers (10, 10) driven by motors (12, 12) are provided. These rollers (10, 10) are spaced apart at a distance less than the distance between the conveyors (6, 6), and rotated in opposing directions so as to compress the dough (2) to provide a dough strip (17) of a thickness K' and to feed it onto an outlet conveyor (14) provided below the rollers (10, 10).

The conveyor (14) is driven by a motor (16). A thickness sensor (18) is provided at an appropriate position to measure the thickness of the dough strip (17) being conveyed on the outlet conveyor (14). Regarding the operation of the sensor (18), please see, to the extent necessary, the explanation on the operation of a thickness sensor (48) that will be given below.

Downstream of the outlet conveyor (14) is provided a first stretching system (19). It comprises a roller mechanism (34), a first conveyor (20), a middle conveyor (30), and a second conveyor (36). The roller mechanism (34) includes a plurality of rollers, and they are rotated in a direction opposite to the advancing direction of the dough strip (17), while revolving along an elliptical path in the same direction as the advancing direction of the dough strip (17). The roller mechanism (34) is driven by a drive unit (not shown), and each roller of the roller mechanism can be rotated by the rolling friction with the dough strip (17) or with a friction board (not shown) provided within the roller mechanism (34). The first conveyor (20) is driven by a motor (22), and a weighing means (24) that comprises a weighing table (28) and a load sensor (26) is provided below the belt of the conveyor (20). The weighing table (28) receives the weight of the dough strip (17) passing over the weighing table (28), and the load sensor (26) senses the weight, converts it into electric signals representative of the weight measured, and sends them through an arrowed line (g) to a computer (not shown) provided in a control unit (49). The computer converts the signals to signals indicating the numerical data of the weight measured, and sends them to a display device (51).

The conveying speeds of the vertical conveyors (6, 6), the conveyor (14) and the conveyor (20), and the peripheral speeds of the rollers (10, 10), are controlled by the control unit (49). The peripheral speeds of the rollers (10, 10) are faster than the conveying speeds of the vertical conveyors (6, 6). The conveying speeds of the conveyor (14) and the conveyor (20) are usually the same as the peripheral speeds of the rollers (10, 10). Electric signals to control the operational speeds of these rollers (10, 10) and conveyors (6, 6, 14, and 20) are sent from the control unit (49) to the motors (12, 12, 8, 8, 16, and 22), through arrowed lines (h, i), (a, b), (c), and (d).

The middle conveyor (30) is provided downstream of the first conveyor (20), and is driven by a motor (32), and its conveying speed is controlled by electric signals from the control unit (49) through an arrowed line (e). The conveying speed of the middle conveyor (30) is somewhat higher than that of the conveyor (20). The second conveyor (36) is provided downstream of the middle conveyor (30), and is driven by a motor (38), and its conveying speed is controlled by electric signals from the control unit (49) through an arrowed line (f). The conveying speed of the second conveyor (36) is somewhat higher than that of the middle conveyor (30).

The weight G, thickness T, and width W, of a portion, passing over the belt (37) of the conveyor (36), of the dough strip (17), the sectional view of which is shown in FIG. 2, are measured by the following means:

A weighing means (60) that comprises a weighing table (62) and a load sensor (64) is provided below the belt of the conveyor (36). The weighing table (62) receives the weight of the dough strip (17) passing over the weighing table (62), and the load sensor (64) senses the weight, converts the data on the weight into electric signals representative of the weight measured, and sends the signals through an arrowed line (j) to the computer in the control unit (49). The signals are then converted into signals indicating the numerical data of the weight measured, and they are sent to the display device (51).

The thickness of the dough strip (17) before it enters the roller mechanism (19) is shown as K'. The thickness is reduced to a thickness K" after it leaves the roller mechanism (19).

A thickness sensor (48) is mounted on a frame (not shown) at a position above the weighing means (60), to measure the thickness of the dough strip (17) being conveyed on the conveyor (36).

In FIG. 3, the dough strip (17) is conveyed on the belt (37) of the conveyor (36). The sensor (48) reciprocates horizontally and transversely above the dough strip (17). The directions of its movement are shown by the arrows m and m'. The sensor (48) emits light and senses its reflections from the surface of the belt (37) and dough strip (17) at each measuring point. These points are spaced apart from the adjacent points by a certain distance m". Vertical lines H indicate the light emitted from the sensor (48) at each measuring point and the reflections from the surface of the belt (37) and dough strip (17). The reflections have distance information showing the distance from the sensor (48) to the belt (37) and dough strip surface. This information is converted into electric signals. These signals are sent to the computer in the control unit (49), where they are converted into signals representative of the height, namely, the thickness of the dough strip (17).

This conversion is carried out by the computer. It subtracts a) the signal representative of the distance from the sensor (48) to the dough strip surface from b) the signal representative of the distance from the sensor (48) to the surface of the belt (37). The computer, upon receiving the signal, calculates the thickness of the dough strip (17) at each measuring point and averages the thickness values measured. The electric signals representative of the averaged thickness value are converted into electric signals indicating numerical data of the thickness, and they are sent to the display device (51).

A width sensor (50) is provided adjacent the sensor (48), as shown in FIG. 1. FIG. 4 illustrates the movement of the width sensor (50). This sensor (50) reciprocates horizontally and transversely above the dough strip (17), and functions like the thickness sensor (48). The reflections from the surface of the dough strip (17) indicate the existence of the dough strip (17), and m" indicates the distance between an adjacent pair of lines H. Therefore, the number of reflections from the surface of the dough is calculated in the computer, and that number is then multiplied by the distance m", in the computer, to obtain electric signals representative of the width of the dough strip (17). These signals are converted into signals indicating the numerical data on the width of the dough strip (17). These signals are sent to the display device (51). The computer calculates the specific weight S of the dough strip passing over the conveyor (36) based on G, W, L, and T, by the following formula:

$$G/(T \times W \times L) = S$$

wherein G represents the weight of the dough strip (17), W represents the width of the dough strip (17), L represents the length of the effective area of the weighing table (62) measured in the advancing direction of the dough strip (17), and T represents the thickness of the dough strip (17).

A second stretching system (33) is provided downstream of these sensors (48, 50) and the weighing means (60). This second stretching system (33) adjusts the thickness of the dough strip (17). This system includes a roller mechanism (40), the second conveyor (36), and a third conveyor (42). The second conveyor (36), functioning as an outlet conveyor of the first stretching system (19), coincidently functions as an inlet conveyor for the second stretching system (33). The conveyor (42) is driven by a motor (44), and the roller mechanism (40) is driven by a driving unit (not shown). The conveying speed of the third conveyor (42) is faster than that of the second conveyor (36). The roller mechanism (40) includes a plurality of rollers, and they rotate in a direction opposite to the advancing direction of the dough strip (17) while revolving along an elliptical path in the same direction as the advancing direction of the dough strip (17). These rollers can be rotated by the rolling friction with the dough strip (17) or with a friction board (not shown) provided within the roller mechanism (40). The conveying speed of the conveyor (42) is controlled by electric signals from the control unit (49) through an arrowed line (k) to the motor (44).

The gap between the conveying path of the conveyor (36) and the lower straight portion of the roller mechanism (40) at its upstream end is somewhat larger than the gap between the conveying path of the conveyor (42) and the lower straight portion of the roller mechanism (40) at its downstream end. These gaps can be adjusted by height adjusting means (46, 46) provided on the two extreme ends of the upper surface of the roller mechanism (40). The height adjusting means (46, 46) can lift or lower the upstream and downstream ends of the mechanism (40) together or separately. The height adjusting means (46, 46) are driven by drive units (not shown), and their operation is controlled by the control unit (49).

Downstream of the mechanism (40) and over the conveying path of the conveyor (42) a puncher (56) for forming a dough piece from the dough strip (17) is provided. Downstream of the conveyor (42) a transferring conveyor (52) is provided. This conveyor (52) is driven by a motor (54), and the conveying speed of the conveyor (52) is controlled by electric signals from the control unit (49) through an arrowed line (n). A rolling-up means (58) for rolling up a dough piece (57) is provided above the conveyor (52).

The operation of the first embodiment of this invention will now be explained.

Raw materials for bread dough, for example, flour, yeast, sugar, shortening, water, etc., are mixed and kneaded in a kneader (not shown) to prepare one lot of a dough mass (2), which is charged into the hopper (4), as shown in FIG. 1. This dough mass (2) is conveyed downstream by the conveyors (6, 6) and is compressed by the rollers (10, 10) and formed into a dough strip (17) having a predetermined thickness. The dough strip (17) is conveyed by the outlet conveyor (14) and the first conveyor (20) and enters the first stretching system (19). When the weight of a portion of the dough strip (17) that passes over the weighing table (28) as measured by the weighing means (24) per unit time deviates from the predetermined reference weight registered in the control unit (49), it sends electric signals (a, b, c, d, h, and i) to the motors to adjust the advancing speed of the dough strip so that the weight per unit is kept generally uniform. The dough strip (17) is then stretched by the first stretching system (19). Since the dough strip (17) is conveyed by the conveyors (20, 30, and 36), and the advancing speed of the strip (17) is incrementally increased, and since the rollers of the roller mechanism (34) hold the dough strip (17) against the three conveyors (20, 30, and 36), the dough strip (17) is increasingly stretched to become a dough strip (17) having a thickness T.

The electric signals representative of the weight, thickness, and width of the dough strip (17) passing over the weighing table (62) are sent to the computer in the control unit (49). These signals are used to calculate the specific weight of portions of the dough strip (17), and are simultaneously converted into signals indicating numerical data. This data is displayed on the screen of the display device (51). Signals representative of the specific weight are also converted into signals indicating the numerical data, and they are also displayed on the screen.

The operator will understand the rheological properties of the dough strip (17) from the data indicated on the display device (51), as follows:

In general, the specific weight of dough depends on the formulation ratio of the raw materials, the kinds of yeast used, or the degree to which the dough is fermented. Therefore, if the specific weight of the dough as displayed on the display device (51) is larger than a predetermined reference value, the operator can change the formulation ratio, the kind of the yeast used, or the fermentation conditions, so that the specific weight of dough in the next lot of the dough mass may be corrected, if needed, to the reference value.

The dimensional data, i.e., the width and thickness of a portion of the dough strip, indicate the rheological properties of the dough strip. These properties substantially depend on the amount of gluten in the dough strip and the water added to the dough mass (2). Namely, if the width value of a portion of the dough strip (17) is greater than, and the thickness value of the same portion is less than, the respective reference values of the dough strip, the portion of the dough strip tends to be more plastic than desired. Therefore, the operator will change the kneading conditions of the next lot of the dough mass so as to increase the gluten in the dough mass, or select flour that includes a larger amount of gluten for the next lot. Also, the operator may plan to decrease the amount of water to be added to the dough mass so as to have the dough mass tend to be more elastic for the next lot of the dough mass.

Also, if the width value of a portion of dough strip (17) is less than, and the thickness value of the same portion is greater than, the respective reference values of the dough strip, the portion of the dough strip tends to be more elastic than desired. Therefore, the operator will change the kneading conditions of the next lot of dough mass so as to decrease the gluten in the dough mass, or to select flour that includes a smaller amount of gluten for the next lot. Also, the operator may plan to increase the amount of water to be added to the dough mass so as to have the dough mass tend to be more plastic for the next lot of the dough mass. Thus, the rheological properties of the next lot of the dough mass will approach the reference values.

A second embodiment of this invention will now be explained by reference to the apparatus in FIG. 1. FIG. 1 was also used to explain the first embodiment.

The dough mass (2) is prepared in the kneader, conveyed by the rollers (6, 6), the rollers (10, 10) and the conveyors (14) and (20), and stretched by the first stretching system (19) to prepare the dough strip (17) having a thickness of T, as in the first embodiment. As will be understood from the discussion regarding the first embodiment, the specific weight of the dough strip (17) tends to be changed for every lot of a dough mass. However, it also tends to fluctuate in the same lot of a dough mass during the operation. Therefore, the specific weight of portions of the dough strip (17) fed from the first stretching system (19) fluctuates. Therefore, when a dough piece (57) having a predetermined area is stamped out from the dough strip (17) by the puncher (56), the weight of the dough piece would also fluctuate, which would lead to end products of inferior quality.

Actually, the bread or confectionery industry usually requires that the weight of the end product always be uniform. Therefore, it is necessary to adjust the thickness of the dough strip to be stamped out so that the weight of a piece of product is always maintained uniform.

To satisfy this requirement, the second stretching system (33) is provided as is mentioned above. If the computer in the control unit (49) detects a signal representative of the specific weight S', it calculates the required thickness T' based on the following formula:

$$T = G'/(S' \times A)$$

wherein T' represents the required thickness of the dough strip (17), G' represents the predetermined reference weight of a dough piece (57), and A represents the area of a dough piece (57) to be stamped out. This area coincides with the bottom area of the puncher (56). When T' is determined, the control unit (49) sends electric signals to operate the height-adjusting means (46, 46). If the specific weight S' is larger than the predetermined reference value, the roller mechanism (40) is lowered, and if less, it is lifted so as to adjust T to T'. When strong plasticity appears in the dough strip (17), its thickness would not smoothly increase in response to the increase in the gap between the roller mechanism and the conveyors (36, 42). Therefore, when the roller mechanism (40) is lifted, the computer in the control unit (49) automatically calculates the conveying speed (V2) of the third conveyor (42) based on the following formula:

$$V2 = (T \times V1)/T$$

Wherein V1 represents the conveying speed of the second conveyor (36).

Then, the control unit (49) sends electric signals representative of V2 through the arrowed line (k) to the motor (44), thereby adjusting the conveying speed of the third conveyor (42) to V2, so that the thickness of the dough strip (17) is adjusted to T'.

Thus, dough pieces (57) each having a uniform weight per unit product can be automatically produced while the thickness of a portion of the dough strip (17) to be stamped out is automatically adjusted so as to make uniform the weight of pieces of the product of uniform dimensions other than the height, in spite of the fluctuation in the specific weight of portions of the dough strip (17).

As was mentioned above, the method of this invention enables the operator in the bread or confectionery industry to inspect, during the operation, the specific weight and the dimensional data of a strip of dough that is continuously fed, and to use them for formulating the composition of the next lot and for processing viscoelastic materials for foodstuffs.

Further, by this invention the weight of unit pieces of viscoelastic materials is made uniform, and this can be attained during a continuous operation, by automatically adjusting the thickness of the pieces, thereby the weight of the pieces can be maintained at the predetermined reference weight.

We claim:

1. A method of controlling the quality of a strip of dough continuously fed from a hopper to a series of conveyor belts, the conveyor belts defining a conveyor path, the conveyor belts conveying the dough strip into a gap between the conveying path and a dough stretching device, the dough strip being stretched between the dough stretching device and the conveyor path, the method comprising:

sensing a thickness, a width and a weight of a portion of said dough strip disposed on the conveyor belts between said hopper and said dough stretching device and producing thickness, width and weight data for said portion;

calculating a specific weight of said portion of said dough strip in response to said thickness, width and weight data, and controlling the gap between the conveying path of the conveyor belts and said dough-stretching device in response to said calculated specific weight such that the thickness of said portion is adjusted to predetermined dimensions and dough pieces uniform in weight may be cut out from said dough strip.

2. A method of claim 1 wherein one or more devices are disposed to process the dough strip prior to the step of sensing, and the method further includes controlling the operating speed of the one or more devices in response to the sensed thickness and weight.

3. A method of claim 1 further comprising the step of processing the dough strip prior to the step of sensing such that the dough strip has a generally uniform thickness.

* * * * *